United States Patent
Honda et al.

(10) Patent No.: US 10,729,737 B2
(45) Date of Patent: Aug. 4, 2020

(54) MUSCLE-ENHANCING AGENT

(71) Applicant: KANEKA CORPORATION, Osaka-shi (JP)

(72) Inventors: Shinichi Honda, Takasago (JP);
Shinichi Yokota, Takasago (JP);
Mineko Ogura, Takasago (JP);
Masanori Kato, Takasago (JP)

(73) Assignee: KANEKA CORPORATION, Osaka-shi (JP)

( * ) Notice: Subject to any disclaimer, the term of this patent is extended or adjusted under 35 U.S.C. 154(b) by 58 days.

(21) Appl. No.: 15/767,189

(22) PCT Filed: Oct. 6, 2016

(86) PCT No.: PCT/JP2016/079757
§ 371 (c)(1),
(2) Date: Apr. 10, 2018

(87) PCT Pub. No.: WO2017/065077
PCT Pub. Date: Apr. 20, 2017

(65) Prior Publication Data
US 2019/0070243 A1    Mar. 7, 2019

(30) Foreign Application Priority Data
Oct. 16, 2015  (JP) .................. 2015-204255

(51) Int. Cl.
*A61K 36/61*   (2006.01)
*A61K 36/00*   (2006.01)
*A23L 33/105*  (2016.01)
*A61P 21/00*   (2006.01)

(52) U.S. Cl.
CPC ............ *A61K 36/61* (2013.01); *A23L 33/105* (2016.08); *A61P 21/00* (2018.01)

(58) Field of Classification Search
None
See application file for complete search history.

(56) References Cited

U.S. PATENT DOCUMENTS

| | | | |
|---|---|---|---|
| 2006/0159828 A1* | 7/2006 | Uehlein | A23F 3/163 426/597 |
| 2009/0281174 A1 | 11/2009 | Ota et al. | |
| 2010/0227002 A1 | 9/2010 | Carta | |
| 2012/0258231 A1 | 10/2012 | Kegasa et al. | |
| 2014/0256653 A1* | 9/2014 | Breuille | A61K 35/20 514/21.2 |
| 2016/0089392 A1* | 3/2016 | Malekian | A23L 29/20 514/4.9 |

FOREIGN PATENT DOCUMENTS

| | | |
|---|---|---|
| CN | 103976987 A | 8/2014 |
| JP | 2008-13473 A | 1/2008 |
| JP | 2009-57325 A | 3/2009 |
| JP | 2010-202520 A | 9/2010 |
| JP | 2010-235542 A | 10/2010 |
| JP | 2012-77010 A | 4/2012 |
| JP | 2013-17467 A | 1/2013 |
| JP | 2013-91608 A | 5/2013 |
| JP | 2015-24982 A | 2/2015 |
| JP | 2015-157785 A | 9/2015 |
| WO | WO 2008/015127 A1 | 2/2008 |

OTHER PUBLICATIONS

Extended European Search Report dated May 24, 2019 in European Patent Application No. 16855331.1, 13 pages.
Southwell, I.A., et al., "*Backhosia citriodora* F. Muell. (Myrtaceae), A Superior Source of Citral", Journal of Essential Oil Research, vol. 12 No. 6, Nov./Dec. 2000, XP055376163, pp. 735-741 with cover page.
International Search Report dated Jan. 10, 2017 in PCT/JP2016/079757 filed Oct. 6, 2016.
Crozier, S. J. et al., "Oral Leucine Administration Stimulates Protein Synthesis in Rat Skeletal Muscle", The Journal of Nutrition, 2005, vol. 135, Issue 3, pp. 376-382.
"Lemon Myrtle Health Benefits" Jessica Jacobs, address :http://healthfully.com/479743-lemon-myrtle-health-benefits.hmtl, pp. 1-3, publication date: Jul. 8, 2011 (3 pages).

* cited by examiner

*Primary Examiner* — Michael Barker
*Assistant Examiner* — Randall Winston
(74) *Attorney, Agent, or Firm* — Oblon, McClelland, Maier & Neustadt, L.L.P.

(57) ABSTRACT

The objective of the present invention is to provide a safe muscle-enhancing agent by which a muscle mass and muscular strength can be effectively increased or maintained and by which a decrease of a muscle mass and muscular strength can be suppressed, a muscle-enhancing composition containing the muscle-enhancing agent, and a method for enhancing muscle by using the muscle-enhancing agent or muscle-enhancing composition. The muscle-enhancing agent according to the present invention is characterized in comprising an extract derived from lemon myrtle as an active ingredient.

12 Claims, No Drawings

MUSCLE-ENHANCING AGENT

TECHNICAL FIELD

The present invention relates to a safe muscle-enhancing agent and a method for enhancing muscle by which a decrease of a muscle mass and a muscular strength can be effectively prevented or treated.

BACKGROUND ART

In recent years, muscle atrophy has become a major problem in association with acceleration of aging and insufficient exercise due to progress in transportation. Muscle atrophy means that a muscle mass and muscular strength are decreased. In general, it is said that a muscle mass and muscular strength are decreased from about 40 years old and many elderly people are in the state of sarcopenia, specifically age-related sarcopenia. Sarcopenia mainly means a decrease in a muscle mass and muscular strength due to aging and is important element of locomotive syndrome and frailty, and it is pointed out that a care need becomes required due to sarcopenia. Locomotive syndrome is referred to as exerciser syndrome, and is an important factor of being in a state of high risk of getting nursing care or becoming a condition to require nursing care by deterioration of mobility function due to a disability of a locomotor apparatus such as muscle, bone, joint, cartilage and intervertebral disc. Frailty means a condition in which muscular strength, mental vitality and physical vitality are deteriorated. Thus, the decrease in a muscle mass and muscular strength lowers not only quality of life (QOL) but also activities of daily living, and closely relates to the occurrence of complications and a greater care burden. In the United States, the decrease in a muscle mass and muscular strength are in the top five health risks, and the related medical expenses are estimated to be about 2.5 trillion yen.

Both of adequate nutritional intake and exercise are required for muscle enhancement, namely increase and maintenance of a muscle mass and muscular strength, as well as suppression of the decrease of a muscle mass and muscle weakness. In case of elderly people, however, a food intake amount tends to be decreased due to loss of appetite and a ratio of an absorption amount to nutrient intake amount tends to be lowered due to a decline in swallowing function, saliva amount and digestive system function. In addition, an efficiency of body function to transform an absorbed peptide or amino acid into muscle protein is also decreased. Furthermore, not only elderly people have less access to exercise but also an increasing efficiency of a muscle mass by an exercise is lowered. As a result, for example, when physical activity of elderly people is decreased due to an injury or disease, a muscle mass and muscular strength are further decreased, and elderly people get trapped into a negative cycle of a decline in physical activity and a deterioration in muscle atrophy.

Muscle enhancement is required for improvement in exercise capacity in sports, prevention and relief of obesity and metabolic syndrome, and slimming. Also, muscle enhancement is required for a non-human animal for the purpose of growth promotion, meat increase and meat quality improvement.

In order to enhance muscle, it is necessary to enlarge or maintain the size of the muscle fiber constituting the muscle. A muscle fiber is a multinucleated cell, and the size of the cell is dependent on the number of the nucleus. Thus, it is necessary to increase the number of nucleus in order to enlarge or maintain a muscle fiber, but the nucleus of a muscle fiber does not increase, and a nucleus has to be supplied into a muscle fiber from the outside of the cell. A nucleus is supplied into a muscle fiber by a myosatellite cell, which exists between the basement membrane and the cell membrane of a muscle cell constituting the muscle. A myosatellite cell is also referred to as a satellite cell. A myosatellite cell is usually in a resting state and undifferentiated, but becomes activated to supply a nucleus into a muscle fiber through processes such as proliferation, differentiation and fusion with a muscle fiber due to exercise, muscle damage and growth. Thus, the activation of a myosatellite cell contributes to muscle enhancement.

Since a decline in a muscle mass and muscular strength progresses with aging as described above, such a decline in a muscle mass and muscular strength should be prevented before becoming obvious. In addition, since elderly people have to continue to take an everyday medicine to suppress chronic disease in some cases, a synthetic medicine has a problem of an unpredictable side effect due to the combination with the everyday medicine.

Accordingly, a safe component having a muscle enhancing action has been searched.

For example, Patent document 1 discloses a muscle senescence inhibitor which contains a catechin contained in a tea drink as an active ingredient. Patent document 2 discloses a muscle-enhancing agent which contains the genus *Salacia* of the family Celastraceae or an extract thereof. A plant of the genus *Salacia* grows wild in India, Sri Lanka and Southeast Asian countries. It is reported in Non-patent document 1 that leucine, which is a branched chain amino acid, has a muscle protein synthesizing action. Patent Document 3 discloses a satellite cell differentiation promoting agent containing Raphuma, which is a plant of the family Amyorae, or an extract thereof; however, Patent Document 3 merely discloses a differentiation inducing effect on a skeletal muscle-derived cell and does not disclose the activation of a myosatellite cell.

Lemon myrtle is an evergreen tree of Myrtaceae family originating in Australia, and the scientific name thereof is *Backhousia citriodora*. Lemon myrtle is a kind of herb, contains a lot of citral as an essential oil component, has a strong refreshing aroma, and is used for cooking. Lemon myrtle has been under study. For example, Patent documents 4 to 6 respectively discloses a whitening composition having a tyrosinase inhibitory action, a skin fibroblast cell growth-promoting agent to prevent or relieve a skin problem due to ultraviolet rays or the like, advanced glycation end products formation inhibitor for preventing or relieving diabetes or diabetes complication which contain lemon myrtle or an extract thereof. On the one hand, an effect of lemon myrtle on muscle has not been studied.

PRIOR ART DOCUMENT

Patent Document

Patent document 1: JP 2008-13473 A

Patent document 2: JP 2010-235542 A

Patent document 3: JP 2012-77010 A

Patent document 4: JP 2009-57325 A

Patent document 5: JP 2010-202520 A

Patent document 6: JP 2015-24982 A

Non-Patent Document

Non-patent document 1: Crozier S J et al, J. Nutr., vol. 135, No. 3, 376-82, 2005

DISCLOSURE OF THE INVENTION

Problems to be Solved by the Invention

As described above, in recent years, a decline in a muscle mass and muscular strength has become a serious problem with the progress of aging society, and the countermeasure is required. Research to increase and maintain a muscle mass and muscular strength has been done; however, an adequate nutrition intake and exercise are merely recommended as an actual measure. An agent for preventing and treating a decline in a muscle mass and muscular strength is being distributed; however, a drug and the like which are safe and which show a sufficient muscle-enhancing effect have not been yet distributed.

The objective of the present invention is to provide a safe muscle-enhancing agent by which a muscle mass and muscular strength can be effectively increased or maintained and by which a decrease of a muscle mass and muscular strength can be suppressed, a muscle-enhancing composition containing the muscle-enhancing agent, and a method for enhancing muscle by using the muscle-enhancing agent or muscle-enhancing composition.

Means for Solving the Problems

The inventors of the present invention made extensive studies to solve the above problems. As a result, the inventors completed the present invention by finding that an extract derived from lemon myrtle is safe and can activate a myosatellite cell, which plays an important role to increase and maintain a muscle mass and muscular strength.

Hereinafter, the present invention is described.

[1] A muscle-enhancing agent, comprising an extract derived from lemon myrtle as an active ingredient.

[2] The muscle-enhancing agent according to the above [1], wherein the extract is extracted from lemon myrtle using water or a mixed solvent of water and a water-miscible solvent.

[3] The muscle-enhancing agent according to the above [1], wherein the extract is extracted from lemon myrtle using water.

[4] The muscle-enhancing agent according to the above [1], wherein the extract is extracted from lemon myrtle using a mixed solvent of water and ethanol.

[5] The muscle-enhancing agent according to any one of the above [1] to [4], wherein the extract is extracted from a leaf of lemon myrtle.

[6] The muscle-enhancing agent according to any one of the above [1] to [5], administered at a dose of 1 mg/kg body weight or more per one day.

[7] A muscle-enhancing composition, comprising the muscle-enhancing agent according to any one of the above [1] to [6].

[8] A method for enhancing muscle, comprising the step of administering the muscle-enhancing agent according to any one of the above [1] to [6] or the muscle-enhancing composition according to the above [7] to an animal.

[9] Use of an extract derived from lemon myrtle for enhancing muscle.

[10] The use according to the above [9], wherein the extract is extracted from lemon myrtle using water or a mixed solvent of water and a water-miscible solvent.

[11] The use according to the above [9], wherein the extract is extracted from lemon myrtle using water.

[12] The use according to the above [9], wherein the extract is extracted from lemon myrtle using a mixed solvent of water and ethanol.

[13] The use according to any one of the above [9] to [12], wherein the extract is extracted from a leaf of lemon myrtle.

[14] The use according to any one of the above [9] to [13], the extract is administered at a dose of 1 mg/kg body weight or more per one day.

[15] A method for enhancing muscle, comprising the step of administering an extract derived from lemon myrtle as an active ingredient.

[16] The method according to the above [15], wherein the extract is extracted from lemon myrtle using water or a mixed solvent of water and a water-miscible solvent. [17] The method according to the above [15], wherein the extract is extracted from lemon myrtle using water.

[18] The muscle-enhancing agent according to the above [15], wherein the extract is extracted from lemon myrtle using a mixed solvent of water and ethanol.

[19] The method according to any one of the above [15] to [18], wherein the extract is extracted from a leaf of lemon myrtle.

[20] The method according to any one of the above [15] to [19], wherein the extract is administered at a dose of 1 mg/kg body weight or more per one day.

Effect of the Invention

The muscle-enhancing agent of the present invention is safe and can be constantly consumed every day, since the active ingredient of the muscle-enhancing agent is an extract of lemon myrtle, which is used for adding flavor to a food in cooking. In addition, since the muscle-enhancing agent exhibits an action to activate a myosatellite cell similarly to exercise, the muscle-enhancing agent can be used for increasing or maintaining a muscle mass and muscular strength and suppressing a decline in a muscle mass and muscular strength.

MODE FOR CARRYING OUT THE INVENTION

The muscle-enhancing agent of the present invention comprises an extract derived from lemon myrtle as an active ingredient. The muscle-enhancing agent of the present invention exhibits a muscle-enhancing action.

The term "muscle-enhancing" in the present invention means that not only a muscle mass and muscular strength is increased or maintained but also a decline of a muscle mass and muscular strength is suppressed. Thus, the "muscle-enhancing agent" of the present invention can be used for increasing or maintaining a muscle mass and muscular strength and further suppressing a decline of a muscle mass and muscular strength. The muscle-enhancing agent of the present invention can be used for enhancing muscle of a healthy people and an athlete who want to enhance muscle and a child and a younger people who need physical development. In addition, the muscle-enhancing agent of the present invention can be used for preventing or relieving a decline in a muscle mass and muscular strength caused by an inaction due to insufficient exercise, long-term laid down condition and plaster cast, malnutrition, sarcopenia, a myopathy such as muscular dystrophy and congenital myopathy, and a neurogenic disease such as amyotrophic lateral sclerosis and spinal muscular atrophy. Furthermore, the muscle-enhancing agent of the present invention can be used for preventing or relieving a condition and disease due to a decline in a muscle mass and muscular strength, such as locomotive syndrome and frailty. Also, the muscle-enhancing agent of the present invention can be used for an animal such as a domestic animal of which growth promotion, an increase in meat amount and an improvement in meat quality are required. The muscle-enhancing agent of the present invention can be also used for preventing or relieving obesity and metabolic syndrome, and for slimming, since muscle can be enhanced by the muscle-enhancing agent of the present invention.

A myosatellite cell is an undifferentiated muscle stem cell which exists between the basement membrane and the cell membrane of a muscle cell constituting muscle. The term "activation of a myosatellite cell" in the present invention means that a myosatellite cell undergoes transition from a resting state to growth phase and supplies a nucleus into a muscle fiber through processes of differentiation and fusion with the muscle fiber. The activation of a myosatellite cell causes a muscle fiber to enlarge and finally enhances muscle, since the number of nuclei which relates to a size of a muscle fiber is increased by the activation of a myosatellite cell. A degree of the activation of a myosatellite cell can be evaluated by measuring the number of the cell, the amount of nucleic acid and the amount of incorporated DNA analog such as bromodeoxyuridine.

Lemon myrtle is an evergreen tree of Myrtaceae family originating in Australia, and the scientific name thereof is *Backhousia citriodora*. In particular, a characteristic aroma is emitted from the leaf, and the essential oil thereof is used as a fragrance.

A raw material part of the lemon myrtle extract is not particularly restricted, and a leaf, stem, root, branch and flower may be used, and a leaf is preferred. A form of the raw material for the extraction is also not particularly restricted, and for example, the form may be a raw state, dried state and pulverized state of the dried material.

The muscle-enhancing agent of the present invention can be produced by the method comprising the step of mixing lemon myrtle and an extraction solvent in order to extract an active ingredient to enhance muscle.

The extraction solvent for obtaining the lemon myrtle extract of the present invention is not particularly restricted, and an aqueous solvent is preferred. The aqueous solvent means water, a water-miscible solvent, and a mixed solvent of water and a water-miscible solvent. The water-miscible solvent is exemplified by a $C_{1-4}$ alcohol such as methanol, ethanol, n-propanol, isopropanol, n-butanol, s-butanol, isobutanol and t-butanol; a ketone solvent such as acetone; an amide solvent such as dimethylformamide and dimethylacetamide; a sulfoxide solvent such as dimethylsulfoxide; a nitrile solvent such as acetonitrile; an organic acid solvent such as acetic acid. The water-miscible solvent is preferably a $C_{2-4}$ alcohol, more preferably a $C_{2-3}$ alcohol, even more preferably ethanol or isopropanol in terms of safety, and particularly preferably ethanol.

As the extraction solvent, water and a mixed solvent of water and a water-miscible solvent are preferred. The upper limit of a ratio of a water-miscible solvent in the mixed solvent is not particularly restricted, and the ratio is preferably 95 v/v % or less, more preferably not more than 90 v/v %, not more than 80 v/v % or not more than 70 v/v %, and even more preferably 60 v/v % or less. The lower limit of the ratio is not also particularly restricted. When the ratio is 0%, in other words, when the extraction solvent is water only, an extract having an excellent effect can be obtained. When an extraction effect by the water-miscible solvent can be expected, the ratio is preferably 5 v/v % or more. In particular, the extraction solvent is preferably 90 v/v % or less aqueous ethanol, more preferably not more than 80 v/v % or not more than 70 v/v % aqueous ethanol, and even more preferably 60 v/v % or less aqueous ethanol.

An amount of the extraction solvent is not particularly restricted and may be appropriately adjusted. The lower limit of the amount is not particularly restricted, and for example, the amount per 1 g of the dried lemon myrtle material or raw lemon myrtle is preferably 1 mL/g or more, more preferably 2 mL/g or more, and even more preferably 3 mL/g or more. The upper limit of the amount is not also particularly restricted, and the amount per 1 g of the dried lemon myrtle material or raw lemon myrtle is preferably 50 mL/g or less, more preferably 20 mL/g or less, and even more preferably 10 mL/g or less.

A temperature for the extraction may be appropriately adjusted. The lower limit of the temperature is not particularly restricted, and the temperature is preferably −20° C. or higher, more preferably 1° C. or higher, and even more preferably 10° C. or higher. The upper limit of the temperature is not also particularly restricted, and the temperature is preferably 121° C. or lower, more preferably 100° C. or lower, and even more preferably 90° C. or lower. When the extraction is performed at a temperature of the boiling point or higher of the used solvent, it is preferred that a vessel for the extraction is sealed or an internal pressure is increased. The extraction solvent may be heated to reflux. The temperature for the extraction may be changed in a step-by-step manner. The extraction may be performed with stirring or in a still standing manner, and may be repeated a plurality of times if needed.

A time for the extraction may be appropriately adjusted. The lower limit of the total time is not particularly restricted, and the time is preferably 5 minutes or longer, more preferably 10 minutes or longer, and even more preferably 30 minutes or longer. The upper limit of the total time is not also particularly restricted, and the time is preferably 48 hours or shorter, more preferably 24 hours or shorter, and even more preferably 10 hours or shorter.

A mixture after the extraction may be directly used, but may be subjected to a general aftertreatment. For example, the extract is separated from the solid extraction residue by filtration or centrifugation, and the separated extract may be dried. For the drying, concentration, drying by heating, spray drying, drying under reduced pressure and freeze dry may be appropriately combined. The separated extract may be sterilized by heat with indirect heating method, direct heating method, electric heating method, microwave heating method or the like. On the one hand, the extract itself, the crude extract or the semipurified extract may be used as long as the extract does not contain an impurity which is inappropriate constituent for a food, drink or medicinal product. Lemon myrtle emits a characteristic odor representatively due to citral, and it is preferred to perform drying procedure such as concentration, drying by heating, spray drying, drying under reduced pressure and freeze dry in order to remove the odor from the lemon myrtle extract.

It is difficult at present to specify which component contained in the lemon myrtle extract of the present invention exerts a muscle-enhancing effect, since the component may not be a main component and an amount of the component is very small, or a plurality of components synergistically behave.

The muscle-enhancing agent of the present invention can be combined with other component to be a muscle-enhancing composition. For example, the lemon myrtle extract itself or the dried lemon myrtle extract itself may be used, and a solution or dispersion in which the dried lemon myrtle extract is dissolved again or dispersed in an appropriate solvent may be used. In addition, the lemon myrtle extract may be formulated. Such a formulation is not particularly restricted, and is exemplified by a tablet, powder, capsule, sugar-coated tablet, granule, liquid and external preparation. A pharmaceutically acceptable additive may be mixed with the muscle-enhancing agent of the present invention depending on a dosage form. Such an additive is exemplified by an excipient, disintegrating agent, lubricant, binder, antioxidant, coloring agent, sweetener, anticoagulant, a dissolution aid for the active ingredient, and stabilizer. The excipient is not particularly restricted, and exemplified by white sugar, lactose, glucose, corn starch, dextrin, mannitol, crystalline cellulose, calcium phosphate, calcium sulfate and magnesium sulfate. The disintegrating agent is not particularly restricted, and exemplified by starch, agar, calcium citrate, calcium carbonate, sodium hydrogencarbonate, dextrin, crystalline cellulose, carboxymethylcellulose and tragacanth. The lubricant is not particularly restricted, and exemplified by talc, magnesium stearate, polyethylene glycol, silica and hydrogenated vegetable oil. The binder is not particularly restricted, and exemplified by ethyl cellulose, methyl cellulose, hydroxypropyl methylcellulose, tragacanth, shellac, gelatin, gum arabic, polyvinylpyrrolidone, polyvinyl alcohol, polyacrylic acid, polymethacrylic acid and sorbitol. The antioxidant is not particularly restricted, and exemplified by ascorbic acid, tocopherol, sodium hydrogen sulfite, sodium thiosulfate, sodium pyrosulfite and citric acid. The coloring agent is not particularly restricted, and exemplified by a coloring agent which is allowed to be added to a medicinal product or food. The sweetener is not particularly restricted, and exemplified by a sweetener which is allowed to be added to a medicinal product or food. The anticoagulant is not particularly restricted, and exemplified by stearic acid, talc, light anhydrous silicic acid and hydrous silicon dioxide. The dissolution aid for the active ingredient is not particularly restricted, and exemplified by an organic acid such as fumaric acid, succinic acid and malic acid. The stabilizer is not particularly restricted, and exemplified by benzoic acid, sodium benzoate, ethyl parahydroxybenzoate and propylene glycol.

The muscle-enhancing composition containing the muscle-enhancing agent of the present invention can be used as, for example, a food, drink, medicinal product, quasi-drug, feed, pet food or drug for animal.

When the muscle-enhancing agent of the present invention is contained in a food such as a food for specified health use, drink, medicinal product, quasi-drug, supplement, feed, pet food or drug for animal, such products may be directly ingested. A form of the muscle-enhancing composition of the present invention may be a formulation for ingestion. Such a formulation for ingestion is exemplified by a form which can be orally administered, such as a capsule, tablet, powder, chewable formulation, syrup and solution. A capsule is exemplified by a hard capsule, microcapsule and soft capsule. A base material of a capsule is not particularly restricted, and is exemplified by carrageenan usable as a food additive, alginic acid derived from seaweed, locust bean gum and guar gum derived from a plant seed, pullulan and curdlan derived from a microorganism, an agent for formulation such as cellulose, in addition to gelatin derived from cattle bone, cow skin, pig skin or fish skin.

The muscle-enhancing agent of the present invention can be added in a general food and drink. A food and drink in which the muscle-enhancing agent of the present invention is contained is not particularly restricted, and is exemplified by a drink such as a milk drink, soft drink, sports drink, nutritional drink, cosmetic drink and liquid nutrient; a sweet stuff such as chewing gum, chocolate, candy, jelly, cake, biscuit and cracker; a frozen dessert such as ice cream; a noodle such as wheat noodle, Chinese noodle, spaghetti and instant noodle; a fish paste cake such as a semicircle-shaped fish paste cake, tube-shaped fish paste cake and boiled flat fish cake; a seasoning such as dressing, mayonnaise and sauce; bread, ham, rice cooker, rice, soup, various retort foods and various frozen foods. The food and drink containing the muscle-enhancing agent of the present invention can be used as a health food, supplement, functional food, food with function claim, dietary supplement, food for specified health use, nutrient function food, nursing care food, smile care diet, chewing/swallowing assisting food, concentrated liquid food and food for sick people. It goes without saying that the muscle-enhancing agent of the present invention can be used in other food form and in a pet food and livestock feed.

A form of the muscle-enhancing composition of the present invention may be a parenteral formulation. For example, the muscle-enhancing composition may be applied to a skin. In such a case, the formulation form is not particularly restricted, and is exemplified by a cream, paste, jelly, gel, emulsion and liquid prepared by dissolving or mixing and dispersing the muscle-enhancing agent of the present invention in a base material, such as an ointment, liniment, lotion and spray; a formulation such as a poultice, prepared dissolving or mixing and dispersing the above-described composition in a base material and applying the obtained solution or dispersion on a support substrate; a formulation such as a plaster and tape, prepared dissolving or mixing and dispersing the above-described composition in an adhesive agent and applying the obtained solution or dispersion on a support substrate.

When the composition of the present invention is used as a quasi-drug, such a quasi-drug is defined in the pharmaceutical affairs law and is exemplified by an oral formulation. Such an oral formulation is exemplified by a liquid formulation such as an extract, elixir, syrup, tincture and limonade, and a solid formulation such as a capsule, granule, pill, powder and tablet.

The muscle-enhancing agent of the present invention exhibits an excellent muscle-enhancing action, such as an ability to activate a myosatellite cell. The action to activate a myosatellite cell can be evaluated by, for example, the following in vitro test. Specifically, a myosatellite cell is isolated from a subject animal and cultivated in a culture medium containing a substance to be tested for 24 hours. Then, bromodeoxyuridine (BrdU) is added thereto so that the final concentration thereof becomes 10 μM, and the mixture is incubated for 2 hours. Next, the myosatellite cell is fixed at 4° C. for 10 minutes using methanol which is cooled with ice and which contains 0.1% $H_2O_2$. After the myosatellite cell is further subjected to DNA denaturation treatment at 37° C. for 1 hour using 2 N hydrochloric acid, a BrdU positive cell is detected by using anti-BrdU antibody as a primary antibody and HRP-conjugated anti-mouse IgG antibody as a secondary antibody and coloring with diaminobenzidine (DAB). A ratio of a BrdU positive cell to a total cell number is calculated as a myosatellite cell activation rate. The myosatellite cell activation rate by the muscle-enhancing agent of the present invention is preferably not less than 42% or not less than 43%, more preferably not less than 44% or not less than 45%, and even more preferably not less than 46% or not less than 48%.

The muscle-enhancing agent of the present invention can be administered to an animal other than a human in addition to a human. Accordingly, the present invention relates to a method for enhancing muscle, characterized in comprising the step of administering the muscle-enhancing agent of the present invention or the muscle-enhancing composition of the present invention to an animal. A subject animal to which the agent or composition is administered is exemplified by a cultured animal, companion animal and competitive animal. A cultured animal is not particularly restricted and is exemplified by a domestic animal such as a horse, cow, pig, sheep, goat, camel and llama; an experimental animal such as a mouse, rat, guinea pig and rabbit; a poultry such as a chicken, duck, turkey and ostrich; a fish; a crustacean; and a shellfish. A companion animal is not particularly restricted and is exemplified by a dog and cat. A competitive animal is not particularly restricted and is exemplified by a racehorse. In this regard, however, a human may be excluded from an animal to which the muscle-enhancing agent of the present invention or the muscle-enhancing composition of the present invention is administered from the issue of a subject matter of a patent.

An administration frequency and dosage amount of the muscle-enhancing agent of the present invention may be appropriately adjusted depending on a subject to be administered, age, sex, condition and the like, and an amount capable of exerting a muscle-enhancing effect is administered to a subject to be administered. For example, the lower limit of the dosage amount to be administered to a human per one day is not particularly restricted, and is preferably 1 mg/kg body weight or more, more preferably 2 mg/kg body weight or more, and even more preferably 3 mg/kg body weight or more. The upper limit of the dosage amount to be administered to a human per one day is not also particularly restricted, and is preferably 50 mg/kg body weight or less, more preferably 40 mg/kg body weight or less, and even more preferably 30 mg/kg body weight or less. A frequency of administration per one day is not particularly restricted, and the agent or composition may be administered in a single dose or in several doses within a desired administration range.

The muscle-enhancing agent of the present invention can be appropriately used in combination with exercise such as resistance exercise, physical therapy, rehabilitation and the like for the purpose of improving the effect of increasing or maintaining a muscle mass and muscular strength. Also, the muscle-enhancing agent of the present invention can be used in combination with other medicine or food having a muscle-enhancing action for the purpose of improving the effect of increasing or maintaining a muscle mass and muscular strength. A food having a muscle-enhancing action is not particularly restricted, and is exemplified by whey protein, whey peptide, casein, casein peptide, soybean protein, soybean peptide, wheat protein, wheat peptide, an amino acid such as valine, leucine, isoleucine, arginine, citrulline and ornithine, creatine, and β-hydroxy-β-methybutyric acid.

The present application claims the benefit of the priority date of Japanese patent application No. 2015-204255 filed on Oct. 16, 2015. All of the contents of the Japanese patent application No. 2015-204255 filed on Oct. 16, 2015, are incorporated by reference herein.

EXAMPLES

Hereinafter, the examples are described to demonstrate the present invention more specifically, but the present invention is in no way restricted by the examples, and the examples can be appropriately modified to be carried out within a range which adapts to the contents of this specification. Such a modified example is also included in the range of the present invention.

Example 1

Preparation of Lemon Myrtle Extract

A dried leaf of lemon myrtle (100 g) was immersed in 500 mL of water or aqueous ethanol shown in Table 1, and the mixture was stirred at 50° C. for 2 hours for extraction. A solid component was separated by filtration to obtain an extraction liquid. The obtained extraction liquid was concentrated under reduced pressure and freeze-dried to remove the solvent and obtain lemon myrtle extract.

TABLE 1

| Extraction solvent | Amount of extract |
| --- | --- |
| water | 16.1 g |
| 20 v/v % ethanol | 20.8 g |
| 40 v/v % ethanol | 24.1 g |
| 60 v/v % ethanol | 24.1 g |
| 80 v/v % ethanol | 18.5 g |
| 90 v/v % ethanol | 12.5 g |
| 95 v/v % ethanol | 10.5 g |
| 99.5 v/v % ethanol | 4.5 g |

Example 2

In Vitro Experiment to Evaluate Ability to Activate Myosatellite Cell (1) Isolation of Myosatellite Cell A femoral muscle tissue was excised from 6 month old male SD rat (Japan SLC, Inc.), and a fat, a connective tissue and the like were removed from the femoral muscle. The femoral muscle was minced, and then treated with 1.25 mg/mL protease aqueous solution (Sigma) at 37° C. for 1 hour. After a myofiber fragment and the like was removed by differential centrifugation, the cell was seeded on a plate which was coated with polylysine (Sigma) and fibronectin (Sigma), and precultured in a 5% $CO_2$ atmosphere at 37° C. for 24 hours. Then, the myosatellite cell was isolated by washing with PBS. As the culture medium, DMEM (Dulbecco's Modified Eagle Medium, Life Technologies) to which 10% horse serum (Life Technologies) was added was used. Hereinafter, the culture medium is abbreviated as "10% HS-DMEM".

(2) Treatment by Substance to be Tested

Each lemon myrtle extract prepared by Example 1 was dissolved or dispersed in water, and the solution or dispersion was added to 10% HS-DMEM in order to obtain 10% HS-DMEM containing the substance to be tested. The culture medium for the isolated myosatellite cell was changed to the 10% HS-DMEM containing the substance to be tested, and the cell was cultivated for 24 hours. The concentration of the substance to be tested was 2.5 μg/mL, and water was used as a control solvent.

(3) Evaluation of Myosatellite Cell Activation

Bromodeoxyuridine (BrdU, Sigma) was added to the culture medium 2 hours before the completion of the cultivation so that the final concentration of BrdU became 10 μM. After the cultivation, the myosatellite cell treated with the substance to be tested was fixed using methanol which was cooled with ice and which contained 0.1% $H_2O_2$ at 4° C. for 10 minutes. After the myosatellite cell was further subjected to DNA denaturation treatment using 2 N hydrochloric acid at 37° C. for 1 hour, a BrdU positive cell was detected by using anti-BrdU antibody (Sigma) as a primary antibody and HRP-conjugated anti-mouse IgG antibody (Sigma) as a secondary antibody and coloring with diaminobenzidine (DAB, Sigma). A ratio of a BrdU positive cell to a total cell number was calculated as a myosatellite cell activation rate. The result is shown in Table 2.

TABLE 2

| Substanbe to be tested | Rate of activated muscle satellite cell |
| --- | --- |
| solvent control | 41.9 ± 1.9% |
| water extract | 50.0 ± 2.1% |
| 20 v/v % ethanol extract | 49.5 ± 2.8% |
| 40 v/v % ethanol extract | 50.3 ± 2.2% |
| 60 v/v % ethanol extract | 47.7 ± 1.9% |
| 80 v/v % ethanol extract | 44.4 ± 0.8% |
| 90 v/v % ethanol extract | 43.2 ± 0.9% |
| 95 v/v % ethanol extract | 42.9 ± 2.0% |
| 99.5 v/v % ethanol extract | 41.5 ± 1.0% |

As the result shown in Table 2, myosatellite cell activation effect of the water extract and 20 to 95 v/v % aqueous ethanol extract derived from lemon myrtle could be clear confirmed in comparison with the solvent control.

Example 3

In Vivo Test to Evaluate Myosatellite Cell Activation Ability (1) Administration of Substance to be Tested Male 14-week old SD rats (Japan SLC, Inc.) were divided into 3 groups of control group, lemon myrtle water extract group and lemon myrtle aqueous ethanol extract group each containing 6 rats. Water, lemon myrtle water extract or lemon myrtle 60 v/v % aqueous ethanol extract was orally administered to each group once a day at a dose of 500 mg/kg body weight for 4 days. Further, bromodeoxyuridine (BrdU, Sigma) was administered intraperitoneally at a dose of 50 mg/kg body weight 2 hours before the dissection.

(2) Isolation of Myosatellite Cell

A femoral muscle tissue was excised from the above-described rat, and a fat, a connective tissue and the like were removed from the femoral muscle. The femoral muscle was minced, and then treated with 1.25 mg/mL protease aqueous solution (Sigma) at 37° C. for 1 hour. After a myofiber fragment and the like was removed by differential centrifugation, the cell was seeded on a plate which was coated with polylysine (Sigma) and fibronectin (Sigma) and precultured in a 5% $CO_2$ atmosphere at 37° C. for 24 hours. Then, the myosatellite cell was isolated by washing with PBS. As the culture medium, 10% HS-DMEM used in the above-described Example 2(1) was used.

(3) Evaluation of Myosatellite Cell Activation

The isolated myosatellite cell was fixed using methanol which was cooled with ice and which contained 0.1% $H_2O_2$ at 4° C. for 10 minutes. After the myosatellite cell was further subjected to DNA denaturation treatment using 2 N hydrochloric acid at 37° C. for 1 hour, a BrdU positive cell was detected by using anti-BrdU antibody (Sigma) as a primary antibody and HRP-conjected anti-mouse IgG antibody (Sigma) as a secondary antibody and coloring with diaminobenzidine (DAB, Sigma). A ratio of a BrdU positive cell to a total cell number was calculated as a myosatellite cell activation rate. Further, a ratio of the myosatellite cell activation rate of each group to the myosatellite cell activation rate of control group was calculated as a myosatellite cell activation degree. The result is shown in Table 3.

TABLE 3

| Group | Muscle satellite cell activation degree |
| --- | --- |
| control group | 1.0 ± 0.4 |
| water extract-administered group | 2.0 ± 0.2* |
| 60 v/v % ethanol extract-administered group | 1.7 ± 0.2* |

As the result shown in Table 3, the ratio of the myosatellite cell activation effects by water extract and 60 v/v % aqueous ethanol extract derived from lemon myrtle to that of the control group were respectively about 2.0 times and about 1.7 times. In accordance with Dunnett test, a significant myosatellite cell activation effect of the water extract-administered group and the 60 v/v % aqueous ethanol-administered group was confirmed with a level of significance of 5% or less. In Table 3, "*" indicates that there is a significant difference to the control group.

The invention claimed is:

1. A method for enhancing muscle, comprising:
   administering from 1 mg/kg body weight to 50 mg/kg body weight per one day of an extract of lemon myrtle to a subject in need thereof, thereby enhancing muscle of the subject,
   wherein the subject having the enhanced muscle has an increased or maintained muscle mass and muscular strength and has a suppressed decline of a muscle mass and muscular strength.

2. The method of claim 1, wherein the extract is extracted from lemon myrtle by using water or a solvent comprising water and a water-miscible solvent.

3. The method of claim 1, wherein the extract is extracted from lemon myrtle by using water.

4. The method of claim 1, wherein the extract is extracted from lemon myrtle by using a solvent comprising water and ethanol.

5. The method of claim 1, wherein the extract is extracted from a leaf of lemon myrtle.

6. The method of claim 4, wherein the solvent comprises 5 v/v % to 90 v/v % of ethanol.

7. The method of claim 4, wherein the solvent comprises 20 v/v % to 60 v/v % of ethanol.

8. The method of claim 1, wherein the extract is orally administered to the subject.

9. The method of claim 1, wherein the extract is parenterally administered to the subject.

10. The method of claim 1, further comprising:
    subjecting the subject to resistance exercise, physical therapy, or rehabilitation.

11. The method of claim 1, further comprising:
    administering to the subject at least one selected from the group consisting of whey protein, whey peptide, casein, casein peptide, soybean protein, soybean peptide, wheat protein, wheat peptide, valine, leucine, isoleucine, arginine, citrulline, ornithine, creatine, and β-hydroxy-β-methylbutyric acid.

12. The method of claim 1, wherein the subject is human, and the extract is administered at a dose of from 3 mg/kg body weight to 30 mg/kg body weight per one day.

* * * * *